US007613275B2

(12) United States Patent
Li et al.

(10) Patent No.: US 7,613,275 B2
(45) Date of Patent: Nov. 3, 2009

(54) METHOD AND APPARATUS FOR REDUCING CONE BEAM ARTIFACTS USING SPATIALLY VARYING WEIGHTING FUNCTIONS

(75) Inventors: Jianying Li, New Berlin, WI (US); Jiang Hsieh, Brookfield, WI (US); Melissa L. Vass, Milwaukee, WI (US); Xiangyang Tang, Waukesha, WI (US); John Howard Londt, Delafield, WI (US); Darin Robert Okerlund, Muskego, WI (US)

(73) Assignee: General Electric Company, Schenectady, NY (US)

( * ) Notice: Subject to any disclaimer, the term of this patent is extended or adjusted under 35 U.S.C. 154(b) by 875 days.

(21) Appl. No.: 11/305,929

(22) Filed: Dec. 19, 2005

(65) Prior Publication Data

US 2007/0140535 A1 Jun. 21, 2007

(51) Int. Cl.
  *A61B 6/00* (2006.01)
(52) U.S. Cl. .............................................. 378/8; 378/4
(58) Field of Classification Search ...................... 378/4, 378/8
  See application file for complete search history.

(56) References Cited

U.S. PATENT DOCUMENTS

| 5,270,923 | A | * | 12/1993 | King et al. ................... 382/131 |
| 5,400,377 | A | | 3/1995 | Hu et al. |
| 5,406,479 | A | | 4/1995 | Harman |
| 5,493,593 | A | | 2/1996 | Muller et al. |
| 5,663,995 | A | | 9/1997 | Hu |
| 5,825,842 | A | * | 10/1998 | Taguchi ...................... 378/15 |
| 5,909,476 | A | | 6/1999 | Cheng et al. |
| 6,009,142 | A | | 12/1999 | Sauer et al. |
| 6,091,840 | A | | 7/2000 | Hu et al. |
| 6,101,236 | A | | 8/2000 | Wang et al. |
| 6,154,516 | A | * | 11/2000 | Heuscher et al. ............. 378/15 |
| 6,243,437 | B1 | * | 6/2001 | Hu et al. ........................ 378/8 |
| 6,408,088 | B1 | | 6/2002 | Hu |
| 6,421,411 | B1 | | 7/2002 | Hsieh |
| 6,426,990 | B1 | | 7/2002 | Cesmeli |
| 6,463,118 | B2 | | 10/2002 | Besson |
| 6,490,333 | B1 | | 12/2002 | Hsieh |

(Continued)

OTHER PUBLICATIONS

Parker, Optimal short scan convolution reconstruction for fanbeam CT, Med Phys, 9, 2, Mar./Apr. 1982, pp. 254-257.*

(Continued)

*Primary Examiner*—Edward J Glick
*Assistant Examiner*—Alexander H Taningco
(74) *Attorney, Agent, or Firm*—The Small Patent Law Group; Dean D. Small

(57) ABSTRACT

A method for combining images acquired using helical half-scan imaging comprises identifying an image plane within an overlap region comprising data from first and second view streams representative of first and second cycles of acquired image data. The image plane comprises the same anatomical structure. First and second weighting functions are calculated for first and second images based on first and second tube positions of an x-ray tube. The first and second images correspond to the image plane and are from the first and second view streams, respectively. The first and second tube positions also correspond to the image plane. A weighted image is then formed based on the first and second weighting functions and the first and second images.

20 Claims, 5 Drawing Sheets

U.S. PATENT DOCUMENTS

| | | |
|---|---|---|
| 6,504,892 B1 | 1/2003 | Ning |
| 6,600,802 B1 | 7/2003 | Hsieh |
| 6,647,095 B2 | 11/2003 | Hsieh |
| 6,678,346 B2 | 1/2004 | Hsieh |
| 6,718,004 B2 | 4/2004 | Cesmeli |
| 6,724,856 B2 | 4/2004 | De Man et al. |
| 6,748,098 B1 | 6/2004 | Rosenfeld |
| 6,771,732 B2 | 8/2004 | Xiao et al. |
| 6,937,690 B2 * | 8/2005 | Bruder et al. ............ 378/15 |

OTHER PUBLICATIONS

Xiangyang Tang, Jiang Hsieh, Roy A. Nilson and Sandeep Dutta, "A helical cone beam filtered backprojection (CB-FBP) reconstruction algorithm using three-dimensional (3D) view weighting", GE Healthcare Technologies, 3000 N. Grandview Blvd., W-1190, Waukesha, WI 53188, USA, 11 pages.

* cited by examiner

METHOD AND APPARATUS FOR REDUCING CONE BEAM ARTIFACTS USING SPATIALLY VARYING WEIGHTING FUNCTIONS

BACKGROUND OF THE INVENTION

This invention relates generally to computed tomography (CT) image processing, and more particularly, to reducing cone beam artifacts in reconstructed images.

Cardiac computed tomography (CT) scans typically use low pitch acquisitions that are retrospectively gated using cardiac EKG signals. Typical multi-slice CT EKG-gated cardiac reconstruction uses half-scan data corresponding to a portion of the cardiac cycle to achieve high temporal resolution needed to reduce cardiac motion. In half-scan mode, projections over the projection angle of $\pi+2\gamma_m$ are used instead of $2\pi$, where $\gamma_m$ is the fan angle of the detector.

To get the necessary coverage of the heart, data is acquired for several heartbeats, with each heart cycle providing data for multiple slices. Data may be acquired helically, although from a reconstruction point of view, the data is similar to data acquired in step-and-shoot mode in that one data stream provides a range of coverage along the Z-axis. For step-and-shoot acquisition mode, it is known that the completely sampled region forms less than a cylindrical disc, or forms an incomplete cylindrical disc, with the disc's height equal to the detector iso-center coverage. Near the source (x-ray tube), the cone beam geometry reduces the coverage of each projection, resulting in a volume which is narrower than the desired volume. Therefore, during reconstruction, a portion of the cylinder that is closer to the source is extrapolated, such as by using the last row of known data in areas lacking data. Extrapolation of data can increase the artifact level significantly for the half-scan case, resulting in distorted structures and undesired shading.

Typically, the helical pitches for cardiac scans are set relatively low to avoid the use of the extreme edge of the detectors in the Z, or patient, direction. The pitch is not set too low to avoid exposing patients to unnecessary radiation. Depending on the application, pitches that allow more than 80% detector usage are selected to balance image quality, coverage and dose.

For a given Z-location during a cardiac helical scan there is a heart cycle whose corresponding detector position is closest to that particular Z-location. Due to the low pitch used during scanning, however, there may be a second heart cycle whose detector positioning covers substantially the same Z-location, though the center of the detector during the second heart cycle may be further away from the imaging location. As image quality degrades with the increase of distance from the center of the detector, the first heart cycle may be used to reconstruct the image using standard single sector reconstruction. Therefore, for Z-locations imaged in more than one heart cycle, a first image of a first Z-location may be preferable from a first heart cycle and a second image of a second Z-location may be preferable from a second heart cycle. With the current single sector reconstruction algorithm, some cone beam artifacts will show up for slices that are closer to the edge of the detector for a specific cardiac cycle.

Therefore, a need exists for reconstructing images while reducing or eliminating cone beam artifacts. Certain embodiments of the present invention are intended to meet these needs and other objectives that will become apparent from the description and drawings set forth below.

BRIEF DESCRIPTION OF THE INVENTION

In one embodiment, a method for combining images acquired using helical half-scan imaging comprises identifying an image plane within an overlap region comprising data from first and second view streams representative of first and second cycles of acquired image data. The image plane comprises the same anatomical structure. First and second weighting functions are calculated for first and second images based on first and second tube positions of an x-ray tube. The first and second images correspond to the image plane and are from the first and second view streams, respectively. The first and second tube positions also correspond to the image plane. A weighted image is formed based on the first and second weighting functions and the first and second images.

In another embodiment, a method for combining computed tomography (CT) images acquired using cone beam geometry comprises identifying first and second images having at least a portion of like anatomical data. The first and second images are acquired within first and second cycles, respectively. Lower weighting functions are applied to first areas of the first and second images and higher weighting functions are applied to second areas of the first and second images. The first areas are closer to x-ray tube locations corresponding to the first and second images and the second areas are further from the x-ray tube locations. A combined image is formed by combining the first and second images with the lower and higher weighting functions.

In another embodiment, a system for combining images comprising like anatomical structure acquired using helical half-scan imaging comprises a computer for receiving image data having at least two cycles of data. The computer is configured to identify an image plane within an overlap region comprising data from first and second view streams representative of first and second cycles of image data. The image plane comprises the same anatomical structure. The computer calculates first and second weighting functions for first and second images based on first and second tube positions of an x-ray tube. The first and second images correspond to the image plane and are from the first and second view streams, respectively. The first and second tube positions correspond to the image plane. The computer forms a weighted image based on the first and second weighting functions and the first and second images.

Figure 1:
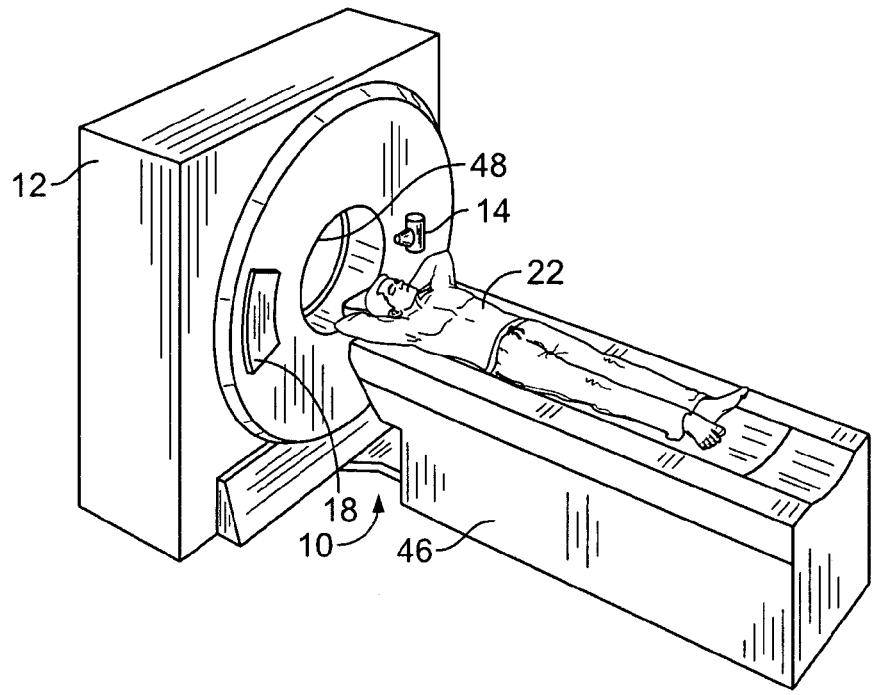
FIG. 1 is a pictorial view of a CT imaging system.

The foregoing summary, as well as the following detailed description of certain embodiments of the present invention, will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

DETAILED DESCRIPTION OF THE INVENTION

Figure 2:
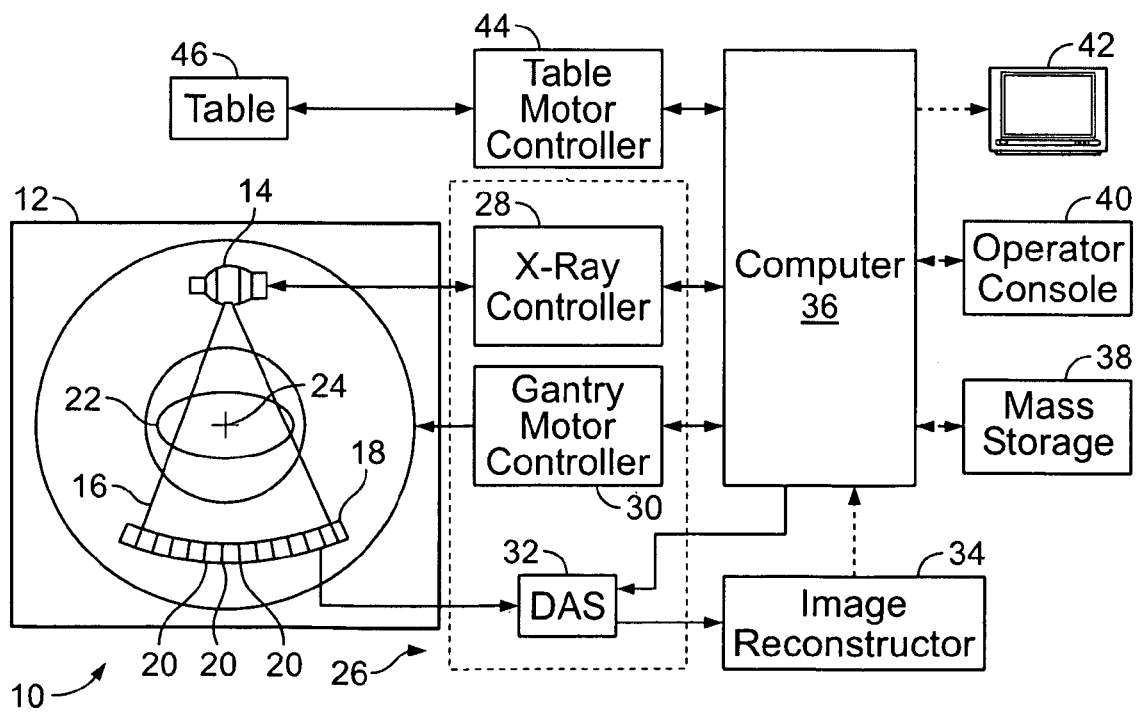
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray tube 14 that projects a beam of x-rays 16 toward a detector array 18 on the opposite side of gantry 12. Detector array 18 is formed by detector elements 20 which together sense the projected x-rays 16 that pass through a patient 22 or object of interest. Each detector element 20 produces an electrical signal that represents the intensity of an impinging x-ray beam and hence the attenuation of the beam as it passes through the patient 22. During a scan to acquire x-ray projection data, gantry 12 and the components mounted thereon rotate about a center of rotation 24.

Rotation of the gantry 12 and the operation of the x-ray tube 14 are governed by a control mechanism 26 of the CT imaging system 10. Control mechanism 26 includes an x-ray controller 28 that provides power and timing signals to x-ray tube 14 and a gantry motor controller 30 that controls the rotational speed and position of gantry 12. A data acquisition system (DAS) 32 in control mechanism 26 samples analog data from detector elements 20 and converts the data to digital signals for subsequent processing.

An image reconstructor 34 receives sampled and digitized x-ray data from DAS 32 and performs high speed image reconstruction. The reconstructed image is applied as an input to a computer 36 which stores the image in a mass storage 38. The reconstructed image may be stored as a data array.

Computer 36 also receives commands and scanning parameters from an operator via console 40 that has input devices such as a keyboard, mouse, touchscreen, microphone for voice commands, and the like. An associated display 42 allows the operator to observe the reconstructed image and other data from computer 36. Commands and parameters supplied by the operator and/or stored in mass storage 38 are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. Other configurations of CT systems may be used, such as a C-arm, a manually operated table, and a mobile unit. Alternatively, the computer 36 may be a stand-alone configuration, typically used for processing, displaying and reviewing image data stored in a storage device, such as mass storage 38, or an optical or compact disc, for example.

The image processing discussed herein is suitable to cardiac images, but may also be used to reconstruct images of other structures. It should be understood that the image processing algorithm may be implemented in computer 36 and would process, for example, image data stored in mass storage 38. Alternatively, the image processing algorithm could be implemented in image reconstructor 34 and supply processed data to computer 36. Other alternative implementations are possible.

Figure 3:
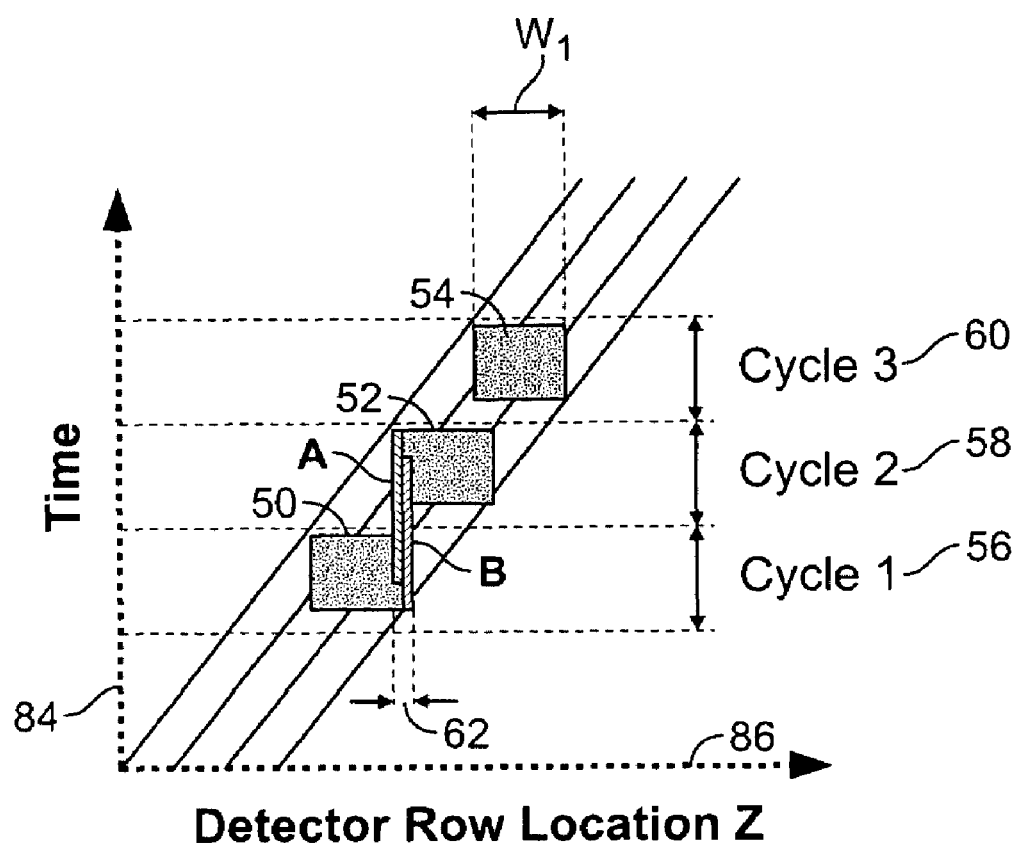
FIG. 3 illustrates a relationship between image locations and cardiac cycles resulting from a half-scan acquisition in accordance with an embodiment of the present invention.

FIG. 3 illustrates a relationship between image locations and cardiac cycles resulting from a half-scan acquisition in accordance with an embodiment of the present invention. First, second and third datasets 50, 52 and 54 are acquired during first, second and third heart cycles 56, 58 and 60, respectively. The Y-axis 84 illustrates time, and the X-axis 86 indicates the detector row location Z, which may also be referred to as the location of the imaged object or reconstructed region of the object. A horizontal width $W_1$ of each dataset 50, 52 and 54 indicates an image region comprising multiple slices. For example, a 64 slice scanner may acquire data from a region of 40 mm. When acquiring half-scan data, the x-ray tube 14 rotates 180 degrees, acquiring approximately 220 degrees of image data within each of the first, second and third datasets 50, 52 and 54.

During the helical scan, the table 46 moves continuously. The first dataset 50 is acquired during the systole or diastole phase of the heart. Then, when the heart is again in systole or diastole phase, a subsequent or second dataset 52 is acquired. Alternatively, the data may be retrospectively gated. That is, the data collection continues for all phases of the cardiac cycle. Image planes A and B indicate an overlap region 62 or common area of the same anatomical structure imaged by both the first and second datasets 50 and 52. For example, the first dataset 50 may comprise 1-40 mm, and the second dataset 52 may comprise 35-75 mm, creating the overlap region 62 between 35-40 mm. It should be understood that FIG. 3 is exemplary and that the overlap region 62 may be larger or smaller than indicated.

Figure 4:
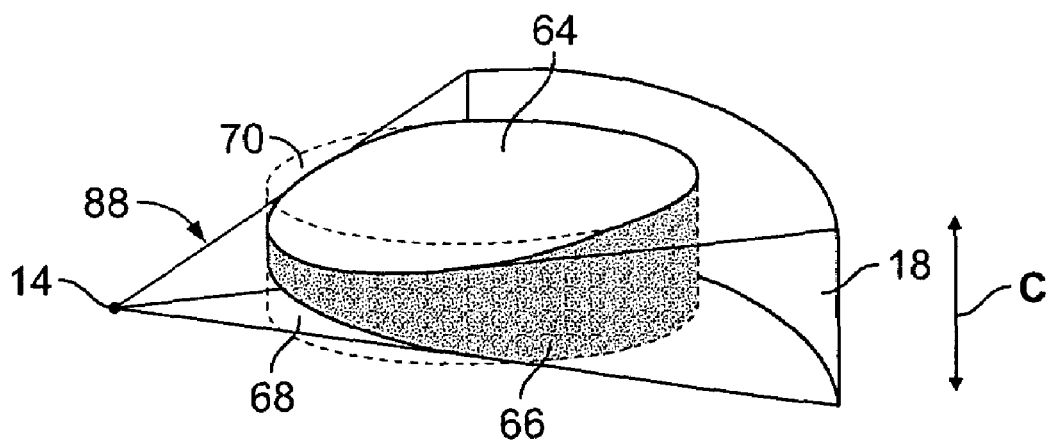
FIG. 4 illustrates a reduction in coverage due to cone beam geometry.

FIG. 4 illustrates a reduction in coverage due to cone beam geometry. A cylindrical disc 64, representing a slice or image, has a shaded area of data 66 and two areas of no data 68 and 70 indicated by dotted lines. The CT projection 88 is cone shaped, so is much narrower in the vertical direction C when closer to the x-ray tube 14 and much wider when closer to the detector array 18. Therefore, there is less coverage for tissue closer to the x-ray tube 14, while full coverage is provided for tissue closer to the detector array 18.

Figure 5:
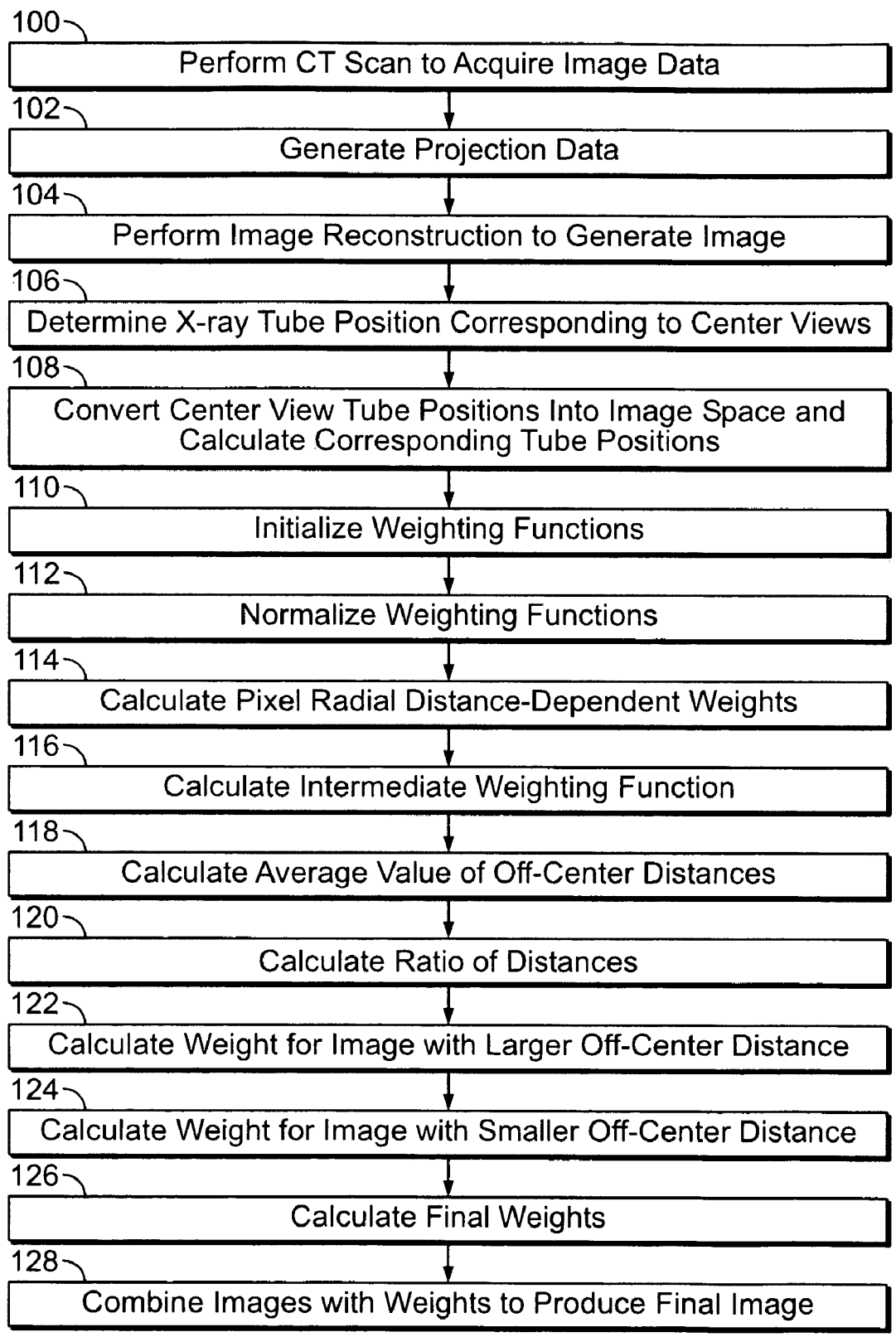
FIG. 5 illustrates a method for combining images of the same anatomical structure with a spatially varying weighting function in accordance with an embodiment of the present invention.

FIG. 5 illustrates a method for combining images of the same anatomical structure with a spatially varying weighting function in accordance with an embodiment of the present invention. The image reconstruction method is discussed with respect to overlapped cardiac helical images acquired using half-scan data and may eliminate and/or reduce cone beam artifacts. By using the redundant data from multiple heartbeats in the overlapped cardiac scans and combining the scans with weights that are dependent upon the x-ray tube 14 location, actual acquired data may be used in the areas of no data 68 and 70 (FIG. 4). Weighting functions may also depend upon the off-center distance and/or the pixel location with respect to the image center. The combination of scans may be done in either projection space or image space. It should be understood that, additionally, non-overlapped scans of the same anatomical structures may also be combined using all or a subset of the steps below.

In step 100, the CT imaging system 10 performs a helical half-scan mode acquisition to acquire helical cardiac image data over more than one heart cycle, such as the first, second and third heart cycles 56, 58 and 60. Data is obtained from the detector elements 20 as previously discussed. In step 102, the image reconstructor 34 generates projection data and in step 104, the image reconstructor 34 performs high speed image reconstruction to generate an image or image data, which may also be referred to as reconstructed view streams wherein each heart cycle has a corresponding reconstructed view stream.

Alternatively, the projection data may be pre-processed, filtered and then backprojected to create the image. Optionally, steps 100, 102 and/or 104 may have been previously accomplished, and the raw, semi-processed, or processed data stored in mass storage 38.

Figure 6:
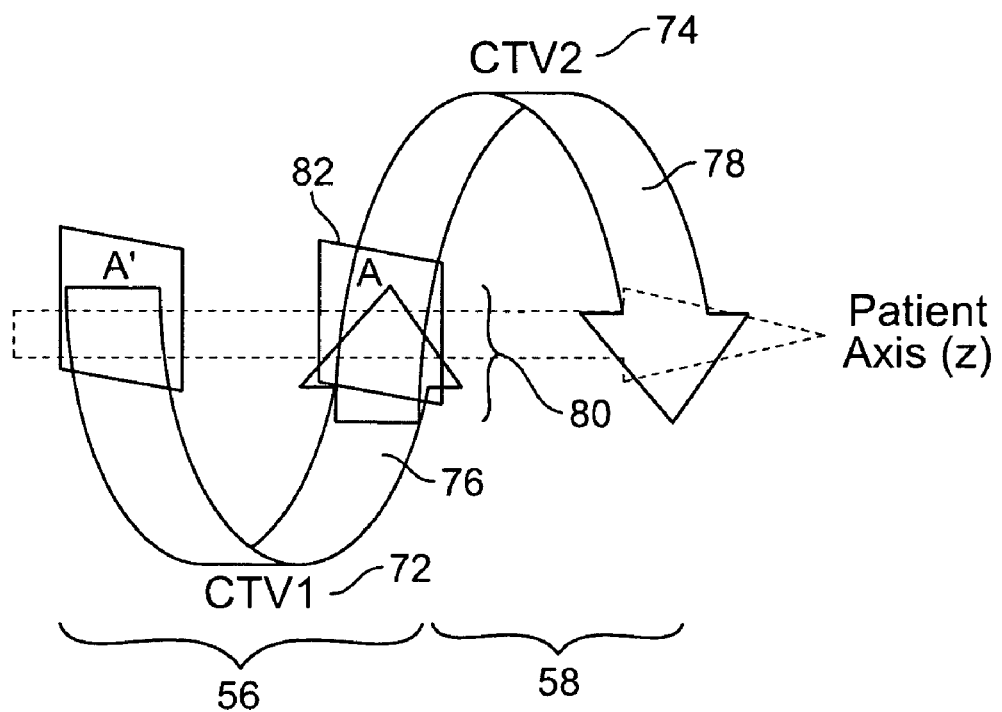
FIG. 6 illustrates a relationship between the image plane A (FIG. 3) and reconstructed data view streams from the first and second heart cycles in accordance with an embodiment of the present invention.

FIG. 6 illustrates a relationship between the image plane A (FIG. 3) and reconstructed data view streams from the first and second heart cycles 56 and 58 in accordance with an embodiment of the present invention. First and second view streams 76 and 78 are indicated as arrows with an overlap region 80. Image plane A comprises data from a portion of the overlap region 80. Detector center views CTV1 72 and CTV2 74 for the first and second view streams 76 and 78, respectively, are indicated.

Returning to FIG. 5, in step 106, the computer 36 determines center view tube positions TPC1 and TPC2 of the x-ray tube 14 for each of the first and second view streams 76 and 78 (FIG. 6) corresponding to the center views CTV1 72 and CTV2 74 of the reconstructed data streams). The computer 36 determines an initial position VTI of the x-ray tube 14 at the beginning of the data acquisition, which is stored in the header of the scan data, the detector center views CTV1 72 and CTV2 74 of the two cardiac cycles and a total number of views per rotation (VPR). Within some imaging systems 10, the x-ray tube initial position VTI may be expressed with a negative value. The center view tube positions TPC1 and TPC2 corresponding to the center views CTV1 72 and CTV2 74 may be calculated using Equation 1:

$$TPC1 = \text{modf}(CTV1/VPR)*360.+abs(VTI)$$

$$TPC2 = \text{modf}(CTV2/VPR)*360.+abs(VTI) \quad \text{Equation 1}$$

where modf(*) denotes the modulo operation, and abs(*) takes the absolute value of the x-ray tube initial position VTI. A center view tube position TPC greater than 360 is reduced by 360 until the value is less than 360.

In step 108, the computer 36 converts the center view tube positions TPC1 and TPC2 into image space and calculates the corresponding tube positions for the image plane A 82. As illustrated in FIG. 6, image plane A 82 is near the edge of the detector coverage in Z and is at the opposite ends of the reconstruction first and second view streams 76 and 78. The identification of the first and second heart cycles 56 and 58 may be based on off-center distances OCD1 and OCD2 between the image plane A 82 and the two center view tube positions TPC1 and TPC2 corresponding to the two center views CTV1 and CTV2. As illustrated, the first heart cycle 56 is the low cycle with positive OCD1 values and the second heart cycle 58 is the high cycle with negative OCD2 values. The tube positions TPA1 and TPA2 for image plane A 82 may be calculated using Equation 2:

$$TPA1=360-TPC1+90 \text{ (for cycle 1)}$$

$$TPA2=360-TPC2-90 \text{ (for cycle 2)} \quad \text{Equation 2}$$

If TPA is greater than 360, then TPA is reduced by subtracting 360. Conversely, if TPA is less than 0, then TPA is converted to positive by adding 360.

Figure 7:
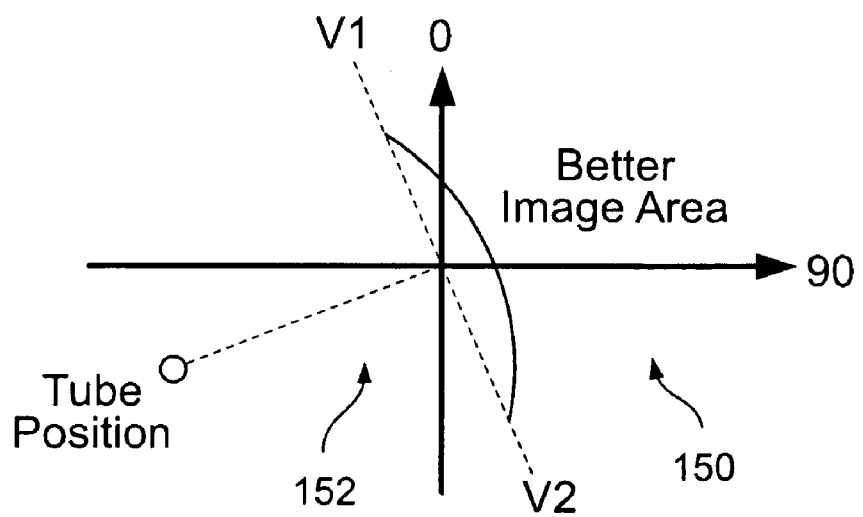
FIG. 7 illustrates a better image area and a tube side area relative to the position of the x-ray tube in accordance with an embodiment of the present invention.

FIG. 7 illustrates a better image area 150 and a tube side area 152 relative to the position of the x-ray tube 14 in accordance with an embodiment of the present invention. As stated previously, areas that are further away from the x-ray tube 14 require less extrapolation and will have better image quality. The better image area 150 may be defined in the image space between angles v1 and v2 that are opposite the x-ray tube 14. Angles v1 and v2 may be calculated for each of the first and second view streams 76 and 78 using Equation 3:

$$v1=TPA+90$$

$$v2=v1+180 \quad \text{Equation 3}$$

Again, if v is greater than 360, the angle is reduced by subtracting 360.

By way of example only, if center view CTV1=1234, center view CTV2=2901, total number of views per rotation VPR=861, and the x-ray tube initial position VTI=−250, then center view tube positions are TPC1=46 degrees and TPC2=23 degrees, and the tube positions for image plane A are TPA1=44 degrees and TPA2=247 degrees. Using the same example, for an image created using the first view stream 76 with the center view CTV1 72, v1 and v2 will be 134 degrees and 314 degrees, respectively. V1 and v2 will be 337 degrees and 157 degrees, respectively, for an image created using the second view stream 78 with the center view CTV2 74.

Figure 8:
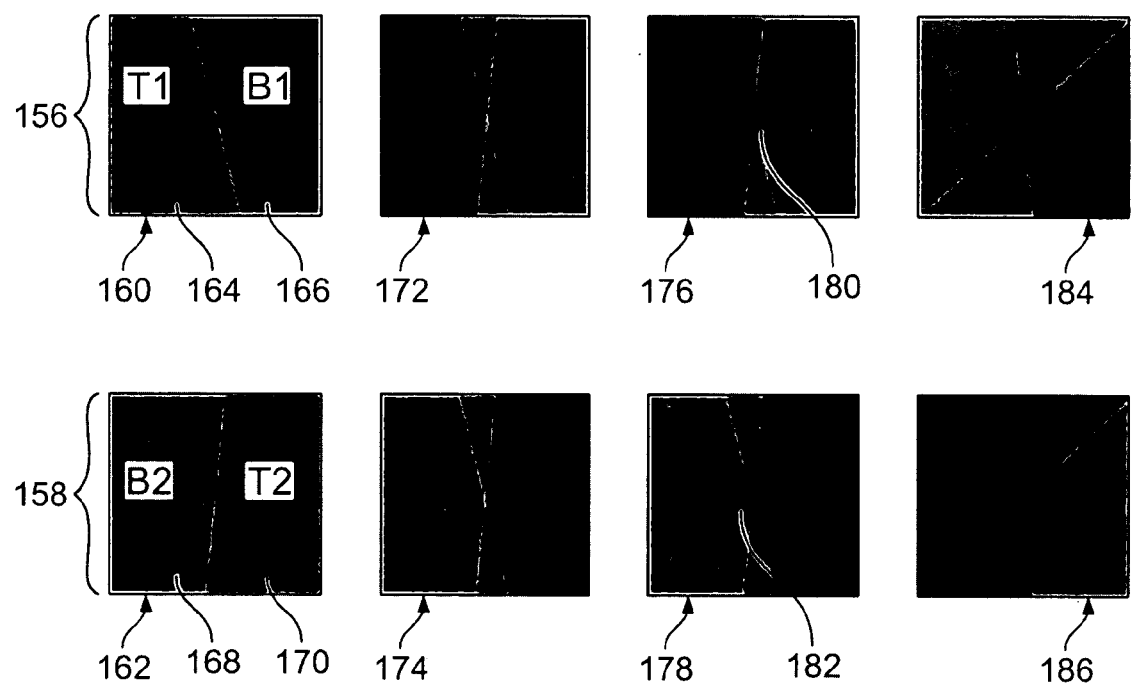
FIG. 8 illustrates an example of weighting functions used when combining first and second images of like anatomy in accordance with an embodiment of the present invention.

FIG. 8 illustrates an example of weighting functions used when combining first and second images of like anatomy in accordance with an embodiment of the present invention. Top row 156 and bottom row 158 illustrate weighting functions for the first and second heart cycles 56 and 58.

Returning to FIG. 5, in step 110, weights for each of the first and second heart cycles 56 and 58 are initialized. The weights for the image from the low cycle (first heart cycle 56) are initialized as weights B1 and T1 for the better image area and the tube side area, respectively. For the image from the high cycle (second heart cycle 58), the corresponding weights are B2 and T2. T1 and T2 may be different depending on respective off-center distances OCD1 and OCD2.

In FIG. 8, tube position weights 160 and 162 are illustrated with shading. From the first heart cycle 56, area 166 corresponds to the better image area B1 and has a higher weighting function than area 164 which corresponds to the tube side area T1. From the second heart cycle 58, area 168 corresponds to the better image area B2 and has a higher weighting function than area 170 which corresponds to the tube side area T2. Therefore, the positions of the x-ray tube 14 in the first and second heart cycles 56 and 58 are approximately opposite.

In step 112, the weighting functions are normalized to 1 on a pixel-by-pixel basis. In FIG. 8, normalized weights 172 and 174 are illustrated. In step 114, pixel radial distance-dependent weighting function WR is calculated to minimize the effect of the tube location-dependent weighting on the central portion of the images. Because cone beam artifacts are less pronounced or not present towards the center of the images, the weighting function may be minimized or excluded from the center area of the image. The pixel radial distance-dependent weighting function WR may be calculated using Equation 4:

$$WR = AR^* \exp(-BR^*(XR/CR)^{\wedge}IR))\qquad\text{Equation 4}$$

where one set of parameters could be AR=10, BR=0.75, CR=2.5, and IR=3.

In step 116, the computer 36 calculates an intermediate weighting function WI. The pixel radial distance-dependent weighting function WR is added to the tube position-dependent weighting function WT, and renormalized to produce the intermediate weighting function WI in Equation 5:

$$WI = (\text{norm}(WT+WR))\qquad\text{Equation 5}$$

In FIG. 8, the intermediate weighting function WI 176 and 178 is illustrated. Center regions 180 and 182 represent the radial exclusion of pixels.

The off-center distances OCD1 and OCD2 discussed previously in step 108 may also be integrated into an overall weighting function. In step 118, the computer 36 calculates an average distance ACD of the two off-center distances OCD1 and OCD2 (between the image plane A 82 and the two detector center views CTV1 72 and CTV2 74) in Equation 6:

$$ACD = (\text{abs}(OCD1)+\text{abs}(OCD2))/2\qquad\text{Equation 6}$$

In step 120, the computer 36 calculates a ratio of the distance between the off-center distance OCD1 and the average distance ACD to slice thickness sck in Equation 7:

$$XD = \text{abs}(OCD1-ACD)/sck\qquad\text{Equation 7}$$

In step 122, the computer 36 calculates a weight WD(larger OCD) for the image with the larger off-center distance using the ratio of Equation 7 in Equation 8:

$$WD(\text{larger } OCD) = AD + BD^*XD\qquad\text{Equation 8}$$

where one set of parameters may be AD=0.5 and BD=−0.16. Negative WD values may be truncated to 0. In this example, the spread is effectively limited to a 3-slice thickness off the average distance ACD. In step 124, the computer 36 calculates a weight WD(smaller OCD) for the smaller off-center distance image with Equation 9:

$$WD(\text{smaller } OCD) = (1-WD(\text{larger } OCD))\qquad\text{Equation 9}$$

Thus, if the two images have the same off-center distance, then the weights for both images will be 0.5.

In step 126, the computer 36 calculates the final weights WF. All weights are normalized to produce the final weights WF and to make sure the sum of the weights from the two images is unity (1) with Equation 10:

$$WF = \text{norm}(WI^*WD)\qquad\text{Equation 10}$$

FIG. 8 illustrates final weights 184 and 186 to be used when calculating the final output images. In step 128, the computer 36 adds the two images representing the same anatomical or physical location from the first and second heart cycles 56 and 58 together with the final weights WF (Equation 10) to produce a final image.

Figure 9:
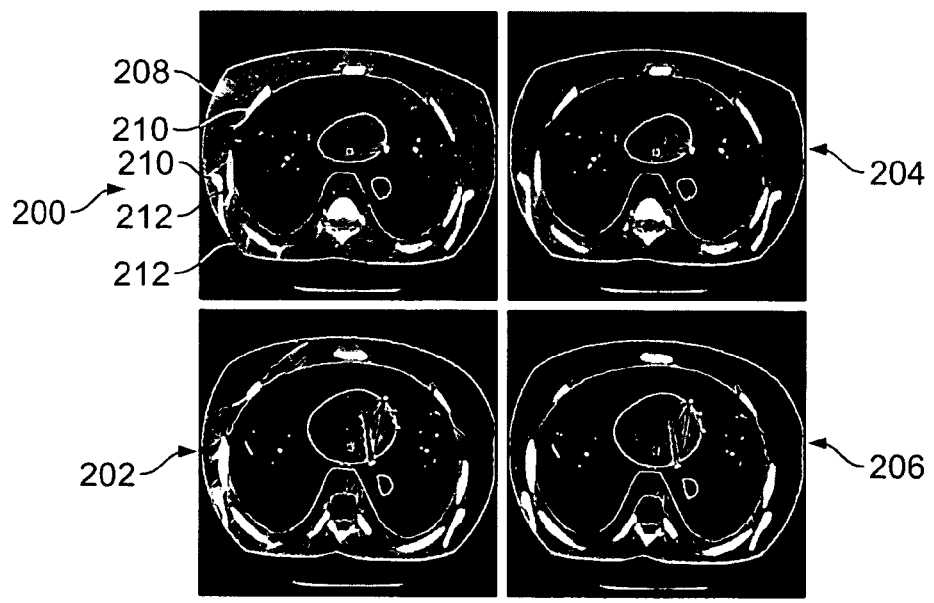
FIG. 9 illustrates a comparison of cardiac phantom images formed in accordance with an embodiment of the present invention.

FIG. 9 illustrates a comparison of cardiac phantom images formed in accordance with an embodiment of the present invention. Images 200 and 202 are reconstructed using single-sector reconstruction. Images 204 and 206 are reconstructed using the spatially varying weighting function of FIG. 5. The images 200, 202, 204 and 206 represent two different images from an overlap region having data from two view streams, such as the overlap region 80 of the first and second view streams 76 and 78 (FIG. 6).

Referring to image 200, cone beam artifacts are present, such as excessive brightness 208 (shown with regard to soft tissue), streaking or distortion 210, and shading 212 (shown with regard to rib structures). By comparing the images 200 and 204, and images 202 and 206, the cone beam artifacts resulting from single-sector reconstruction are eliminated or significantly reduced when images are instead combined using the spatially varying weighting function. Therefore, the image comparison clearly demonstrates the benefit of combining images of like anatomical structures with spatially varying weighting functions.

A technical effect is providing a method to combine overlapped helical cardiac half-scan images with a spatially varying weighting function to reduce cone beam artifacts. As a result, more detector areas may be used for patient data, allowing more dose efficient cardiac scans. Images may be combined with spatially varying weighting functions that are dependent on the position of the x-ray tube 14. Additionally, weighting functions may be used to minimize impact on the center portion of the images and may also depend on the off-center distance. The combining method may also be applied to non-overlapped scans of the same anatomical structures.

While the invention has been described in terms of various specific embodiments, those skilled in the art will recognize that the invention can be practiced with modification within the spirit and scope of the claims.

What is claimed is:

1. A method for combining images acquired using helical half-scan imaging, comprising:
    identifying an image plane within an overlap region comprising data from first and second view streams representative of first and second cycles of acquired image data, the image plane comprising the same anatomical structure;
    calculating first and second weighting functions for first and second images based on first and second tube positions of an x-ray tube, the first and second images corresponding to the image plane and being from the first and second view streams, respectively, the first and second tube positions corresponding to the image plane; and
    forming a weighted image based on the first and second weighting functions and the first and second images.

2. The method of claim 1, the first and second weighting functions further comprising a pixel radial distance-dependent weighting function for minimizing the first and second weighting functions within a portion of the first and second images.

3. The method of claim 1, further comprising:
    calculating lower weights for tube side areas within the first and second images closer to the x-ray tube; and
    calculating higher weights for better image areas within the first and second images further from the x-ray tube, the first and second weighting functions being based on the lower and higher weights.

4. The method of claim 1, further comprising:
    defining a center area based on the first and second images; and
    calculating a pixel radial distance-dependent weighting function for the center area, the pixel radial distance-dependent weighting function minimizing change to the center area by the first and second weighting functions.

5. The method of claim 1, further comprising calculating a center view tube position based on at least one of an initial position of the x-ray tube at the beginning of a scan, first and second center views of the first and second cycles, and a total number of views per rotation, the first and second tube positions being further calculated based on the center view tube position.

6. The method of claim 1, wherein the first and second cycles comprising consecutive heart cycles.

7. The method of claim 1, further comprising identifying third and fourth images within the first and second view streams, respectively, the third and fourth images comprising the same anatomical structure with respect to each other, the third and fourth images forming a non-overlapped region.

8. A method for combining computed tomography (CT) images acquired using cone beam geometry, comprising:
identifying first and second datasets comprising at least a portion of like anatomical data, the first and second datasets being acquired within first and second cycles, respectively;
applying lower weighting functions to first areas of the first and second datasets and higher weighting functions to second areas of the first and second datasets, the first areas being closer to x-ray tube locations corresponding to the first and second datasets and the second areas being further from the x-ray tube locations; and
forming a combined image by combining the first and second datasets with the lower and higher weighting functions.

9. The method of claim 8, further comprising:
identifying an area of pixels within a center region of the first and second datasets; and
calculating a pixel radial distance-dependent weighting function for minimizing the lower and higher weighting functions within the center region.

10. The method of claim 8, further comprising:
calculating a center view tube position based on at least one of an initial position of an x-ray tube at the beginning of a scan, first and second center views of the first and second cycles, respectively, and a total number of views per rotation; and
calculating first and second tube positions of the x-ray tube corresponding to the first and second datasets and being based on the center view tube position, the first and second areas being further defined by the first and second tube positions.

11. The method of claim 8, further comprising identifying third and fourth datasets within the first and second cycles, respectively, the third and fourth datasets comprising the same anatomical data, the third and fourth datasets forming a non-overlapped region.

12. The method of claim 8, further comprising normalizing the lower and higher weighting functions.

13. The method of claim 8, further comprising:
identifying first and second detector center views and first and second x-ray tube initial positions based on the first and second cycles, respectively; and
calculating first and second center view tube positions based on the first and second detector center views and the first and second x-ray tube initial positions, the first and second areas being further based on the first and second center view tube positions.

14. The method of claim 8, further comprising:
identifying first and second detector center views based on the first and second cycles; and
calculating a first off-center distance between the first dataset and the first detector center view and a second off-center distance between the second dataset and the second detector center view, the lower and higher weighting functions being further based on the first and second off-center distances.

15. A system for combining images comprising like anatomical structure acquired using helical half-scan imaging, the system comprising:
a computer for receiving image data comprising at least two cycles of data, the computer configured to:
identify an image plane within an overlap region comprising data from first and second view streams representative of first and second cycles of image data, the image plane comprising substantially the same anatomical structure;
calculate first and second weighting functions for first and second images based on first and second tube positions of an x-ray tube, the first and second images corresponding to the image plane and being from the first and second view streams, respectively, the first and second tube positions corresponding to the image plane; and
form a weighted image based on the first and second weighting functions and the first and second images.

16. The system of claim 15, the computer further configured to:
calculate lower weights for tube side areas within the first and second images closer to the x-ray tube; and
calculate higher weights for better image areas within the first and second images further from the x-ray tube, the first and second weighting functions being based on the lower and higher weights.

17. The system of claim 15, the computer further configured to:
define a center area based on the first and second images; and
calculate a pixel radial distance-dependent weighting function for the center area, the pixel radial distance-dependent weighting function minimizing change to the center area by the first and second weighting functions.

18. The system of claim 15, the computer further configured to normalize the first and second weighting functions.

19. The system of claim 15, the computer further configured to:
identify first and second detector center views and first and second x-ray tube initial positions based on the first and second cycles, respectively; and
calculate first and second center view tube positions based on the first and second detector center views and the first and second x-ray tube initial positions, the first and second tube positions being based on the first and second center view tube positions.

20. The system of claim 15, the computer further configured to:
identify first and second detector center views based on the first and second cycles; and
calculate a first off-center distance between the first image and the first detector center view and a second off-center distance between the second image and the second detector center view, the first and second weighting functions being further based on the first and second off-center distances, respectively.

* * * * *

UNITED STATES PATENT AND TRADEMARK OFFICE
CERTIFICATE OF CORRECTION

PATENT NO.       : 7,613,275 B2                                      Page 1 of 1
APPLICATION NO. : 11/305929
DATED            : November 3, 2009
INVENTOR(S)      : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 988 days.

Signed and Sealed this

Nineteenth Day of October, 2010

David J. Kappos
*Director of the United States Patent and Trademark Office*